US00PP32641P2

(12) United States Plant Patent
Miller

(10) Patent No.: US PP32,641 P2
(45) Date of Patent: Dec. 15, 2020

(54) ***PETUNIA* PLANT NAMED 'BBTUN91601M2'**

(50) Latin Name: ***Petunia* X *hybrida***
Varietal Denomination: BBTUN91601M2

(71) Applicant: Josh Miller, Petersburg, MI (US)

(72) Inventor: Josh Miller, Petersburg, MI (US)

(73) Assignee: PLANT 21 LLC, Bonsall, CA (US)

( * ) Notice: Subject to any disclaimer, the term of this patent is extended or adjusted under 35 U.S.C. 154(b) by 0 days.

(21) Appl. No.: 16/873,586

(22) Filed: May 14, 2020

(30) Foreign Application Priority Data

May 17, 2019 (CA) ..... PBR 19-9877

(51) Int. Cl.
*A01H 5/02* (2018.01)
*A01H 6/82* (2018.01)

(52) U.S. Cl.
USPC ..... Plt./356.13
CPC ..... *A01H 6/824* (2018.05)

(58) Field of Classification Search
USPC ..... Plt./263.1, 356.1, 356.13
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct *Petunia* plant named 'BBTUN91601M2', characterized by its upright to outwardly spreading and mounding to eventually trailing plant habit; vigorous growth habit and rapid growth rate; freely branching habit; dense and bushy plant form; early and freely flowering habit; dark red purple and white bi-colored flowers; and excellent garden performance.

1 Drawing Sheet

Botanical designation: *Petunia* X *hybrida*.
Cultivar denomination: 'BBTUN91601M2'.

CROSS-REFERENCE TO A RELATED APPLICATION AND STATEMENT REGARDING PRIOR DISCLOSURES BY INVENTOR/APPLICANT

This application claims priority to a Canadian Plant Breeders' Rights application filed on May 17, 2019, application number 19-9877. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Petunia* plant, botanically known as *Petunia* X *hybrida* and hereinafter referred to by the name 'BBTUN91601M2'.

The new *Petunia* plant is a naturally-occurring branch mutation of *Petunia* X *hybrida* 'USTUN91601', disclosed in U.S. Plant Pat. No. 29,663. The new *Petunia* plant was discovered by the Inventor on a single flowering plant from within a population of plants of 'BBTUN91601' in a controlled greenhouse environment in Carleton, Mich. on Aug. 15, 2017.

Asexual reproduction of the new *Petunia* plant by vegetative terminal cuttings in a controlled greenhouse environment in Carleton, Mich. since Aug. 15, 2017 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BBTUN91601M2'. These characteristics in combination distinguish 'BBTUN91601M2' as a new and distinct *Petunia* plant:

1. Upright to outwardly spreading and mounding to eventually trailing plant habit.
2. Vigorous growth habit and rapid growth rate.
3. Freely branching habit; dense and bushy plant form.
4. Early and freely flowering habit.
5. Dark red purple and white bi-colored flowers.
6. Excellent garden performance.

Plants of the new *Petunia* can be compared to plants of the mutation parent, 'USTUN91601'. In side-by-side comparisons, plants of the new *Petunia* differ primarily from plants of 'USTUN91601' in plant and growth habit as plants of the new *Petunia* are more freely branching, denser and more uniformly mounding than plants of 'USTUN91601'.

Plants of the new *Petunia* can be compared to plants of 'Kakegawa S36', disclosed in U.S. Plant Pat. No. 14,037. In side-by-side comparisons, plants of the new *Petunia* differ primarily from plants of 'Kakegawa S36' in the following characteristics:

1. Plants of the new *Petunia* are more mounding than and not as trailing as plants of 'Kakegawa S36'.
2. Plants of the new *Petunia* flower earlier than plants of 'Kakegawa S36'.
3. Plants of the new *Petunia* and 'Kakegawa S36' differ in flower color as plants of the new *Petunia* have dark red purple and white bi-colored flowers whereas plants of 'Kakegawa S36' have solid magenta-colored flowers.
4. Plants of the new *Petunia* have improved pathogen tolerance than plants of 'Kakegawa S36'.

Plants of the new *Petunia* can also be compared to plants of 'KL 1117', disclosed in U.S. Plant Pat. No. 25,485. In side-by-side comparisons, plants of the new *Petunia* differ primarily from plants of 'KL 1117' in the following characteristics:

1. Plants of the new *Petunia* are more mounding than and not as trailing as plants of 'KL 1117'.
2. Plants of the new *Petunia* flower earlier than plants of 'KL 1117'.
3. Plants of the new *Petunia* and 'KL 1117' differ in flower color as plants of the new *Petunia* have dark red purple and white bi-colored flowers whereas plants of 'KL 1117' have white-colored flowers.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

At the top of the photographic sheet (FIG. 1) is a side perspective view of a typical flowering plant of 'BBTUN91601M2' grown in a container and at the bottom of the photographic sheet is a close-up view of a typical flowering plant of 'BBTUN91601M2'.

DETAILED BOTANICAL DESCRIPTION

The aforementioned photographs and following observations and measurements describe plants grown during the spring in 15.25-cm containers in a polyethylene-covered greenhouse in St. Thomas, Ontario, Canada and under cultural practices typical of commercial *Petunia* production. During the production of the plants, day temperatures averaged 27° C. and night temperatures averaged 15° C. Plants were pinched three weeks after planting and were ten weeks from planting rooted cuttings when the photographs and description were taken. In the following description, color references are made to The Royal Horticultural Society Colour Chart, 2007 Edition, except where general terms of ordinary dictionary significance are used.

Botanical classification: *Petunia* X *hybrida* 'BBTUN91601M2'.

Parentage: Naturally-occurring branch mutation of *Petunia* X *hybrida* 'USTUN91601', disclosed in U.S. Plant Pat. No. 29,663.

Propagation:

*Type*.—Terminal vegetative cuttings.

*Time to initiate roots, summer*.—About three to four days at ambient temperatures ranging from 17° C. to 29° C.

*Time to initiate roots, winter*.—About five to seven days at ambient temperatures ranging from 17° C. to 21° C.

*Time to produce a rooted plant, summer*.—About three weeks at ambient temperatures ranging from 17° C. to 29° C.

*Time to produce a rooted plant, winter*.—About four weeks at ambient temperatures ranging from 17° C. to 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright to outwardly spreading and mounding to eventually trailing plant habit; freely branching habit with about six primary lateral branches each with about eight secondary branches developing per plant, dense and bushy plant form; pinching enhances development of lateral branches; vigorous growth habit and rapid growth rate.

*Plant height*.—About 20.6 cm.

*Plant diameter* (*area of spread*).—About 61.4 cm.

*Lateral branches*.—Length: About 17.7 cm. Diameter: About 2 mm. Internode length: About 2 cm. Strength: Moderately strong; flexible, not brittle. Aspect: Initially upright then outwardly spreading to almost horizontal and eventually trailing. Texture and luster: Moderately pubescent; matte. Color, developing: Close to 144A. Color, developed: Close to 146B.

Leaf description:

*Arrangement*.—Alternate before flowering; opposite after flowers develop; leaves simple.

*Length*.—About 4.2 cm.

*Width*.—About 2.4 cm.

*Shape*.—Ovate to elliptic.

*Apex*.—Acute.

*Base*.—Obtuse.

*Margin*.—Entire, not undulate.

*Texture and luster, upper and lower surfaces*.—Sparsely pubescent; matte.

*Venation pattern*.—Pinnate, arcuate.

*Color*.—Developing leaves, upper surface: Close to 137A. Developing, lower surface: Close to 138B. Fully developed leaves, upper surface: Close to 137A; venation, close to N144C. Fully developed leaves, lower surface: More green than 147B; venation, close to 143C.

*Petioles*.—Length: About 6 mm. Diameter: About 3.5 mm. Strength: Moderately strong, flexible. Texture and luster, upper and lower surfaces: Slightly pubescent; matte. Color, upper and lower surfaces: Close to 144B.

Flower description:

*Flower type and flowering habit*.—Single terminal and axillary salverform flowers; flowers face mostly upward to outwardly; freely flowering habit with about 150 flower buds and open flowers per plant at one time.

*Natural flowering season*.—Long day responsive; long flowering period, plants flower from early spring until frost in the autumn, flowering continuous during this period; early flowering habit, plants begin flowering about six weeks after planting.

*Flower longevity on the plant*.—About five to seven days; flowers not persistent.

*Fragrance*.—Faint; sweet, pleasant.

*Flower buds*.—Length: About 3 cm. Diameter: About 5 mm. Shape: Oblong, elongate. Texture and luster: Densely pubescent; matte. Color, sepals: Close to 138A. Color, petals: Close to 83B; towards the apex, close to N77B.

*Flower diameter*.—About 4.5 cm.

*Flower depth* (*height*).—About 3.3 cm.

*Throat diameter, distal*.—About 8 mm.

*Tube length*.—About 2.2 cm.

*Tube diameter, distally*.—About 8 mm.

*Tube diameter, proximally*.—About 2 mm.

*Petals*.—Quantity and arrangement: Five petals fused in a single salverform whorl. Petal lobe length (from throat): About 2 cm. Petal lobe width: About 2.4 cm. Petal lobe shape: Spatulate. Petal lobe apex: Cuspidate. Petal lobe margin: Entire; moderately undulate. Petal lobe texture and luster, upper surface: Smooth, glabrous; velvety; matte. Petal lobe texture and luster, lower surface: Densely pubescent; matte. Throat texture and luster: Smooth, glabrous; matte. Tube texture and luster: Moderately pubescent; matte. Color: When opening, upper surface: Darker than N74A. When opening, lower surface: Close to 77B. Fully opened, upper surface: More purple than N74A; towards the margins, close to NN155C; venation, darker than N74A; color does not change with development. Fully opened, lower surface: Close to N78C; towards the margins, close to NN155C; venation, close to N78B and N186C; with development, colors becoming closer to more purple than N74B and NN155C. Flower throat (inside): Close to 76B; venation, close to N92A and 76B. Flower tube (outside): Close to N78C; venation, close to 146C.

*Sepals*.—Quantity and arrangement: Five sepals fused in a single star-shaped whorl. Length: About 1.1 cm. Width: About 3 mm. Shape: Oblanceolate. Apex: Bluntly acute. Margin: Entire. Texture and luster, upper and lower surfaces: Moderately pubescent; matte. Color: When opening and fully developed, upper surface: Close to 137A. When opening and fully developed, lower surface: Close to 138A.

*Peduncles*.—Length: About 2.5 cm. Width: About 1 mm. Strength: Moderately strong; wiry and flexible, not brittle. Angle: About 45° to 90° from stem axis. Texture and luster: Densely pubescent; matte. Color: Close to 144A; distally, close to N77C.

*Reproductive organs*.—Stamens: Quantity per flower: Five. Filament length: About 2.1 cm. Filament color: Close to 145D. Anther length: About 1.4 mm. Anther shape: Bi-lobed. Anther color: Close to 97C. Pollen amount: Abundant. Pollen color: Close to 98D. Pistils: Quantity per flower: One. Pistil length: About 1.8 cm. Style length: About 1.7 cm. Style color: Close to N155D. Stigma diameter: About 1.7 mm. Stigma shape: Round. Stigma color: Close to 144B. Ovary color: Close to 144A.

*Seeds and fruits*.—To date, seed and fruit development has not been observed on plants of the new *Petunia*.

Pathogen & pest resistance: To date, plants of the new *Petunia* have not been noted to be resistant to pathogens or pests common to *Petunia* plants.

Garden performance: Plants of the new *Petunia* have been observed to have excellent garden performance and have been observed to tolerate rain, wind and temperatures ranging from about 1° C. to about 40° C.

It is claimed:

1. A new and distinct *Petunia* plant named 'BBTUN91601M2' as illustrated and described.

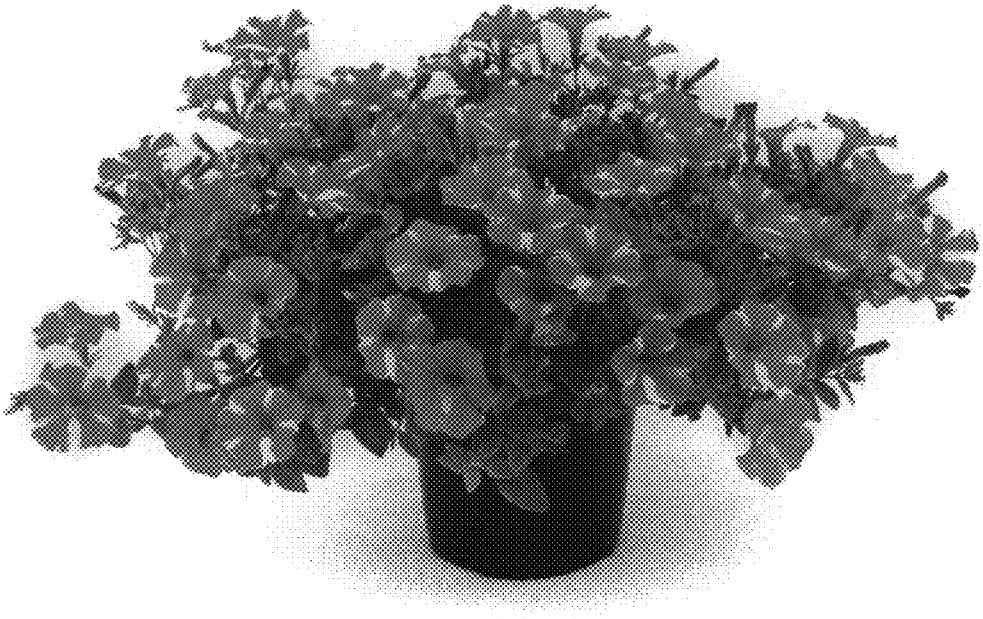
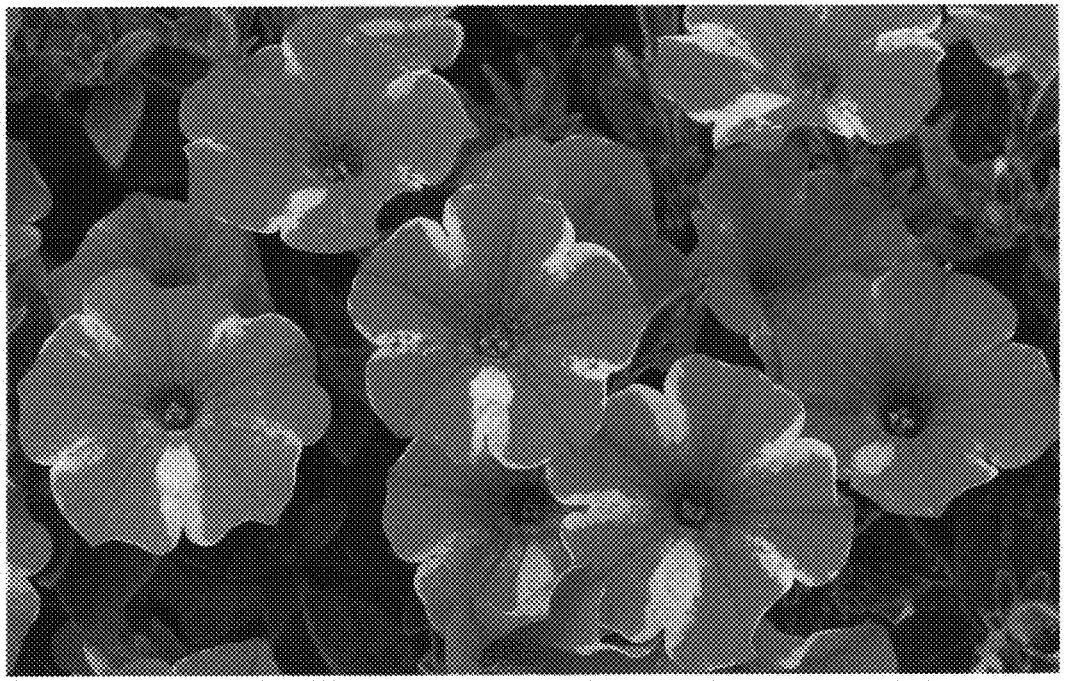

* * * * *